(12) United States Patent
Zografos et al.

(10) Patent No.: US 10,962,512 B2
(45) Date of Patent: Mar. 30, 2021

(54) PATHOGEN SURROGATES BASED ON ENCAPSULATED TAGGED DNA FOR VERIFICATION OF SANITATION AND WASH WATER SYSTEMS FOR FRESH PRODUCE

(71) Applicant: SafeTraces, Inc., Oakland, CA (US)

(72) Inventors: Antonios Zografos, Oakland, CA (US); George Roy Farquar, Livermore, CA (US); John Mark Carter, Livermore, CA (US)

(73) Assignee: Safetraces, Inc., Oakland, CA (US)

(*) Notice: Subject to any disclaimer, the term of this patent is extended or adjusted under 35 U.S.C. 154(b) by 334 days.

(21) Appl. No.: 15/053,731

(22) Filed: Feb. 25, 2016

(65) Prior Publication Data
US 2017/0038353 A1 Feb. 9, 2017

Related U.S. Application Data

(60) Provisional application No. 62/200,456, filed on Aug. 3, 2015.

(51) Int. Cl.
*G01N 31/22* (2006.01)
*A61L 2/28* (2006.01)
(Continued)

(52) U.S. Cl.
CPC .............. *G01N 31/226* (2013.01); *A61L 2/28* (2013.01); *C07H 21/04* (2013.01); *C07K 14/78* (2013.01);
(Continued)

(58) Field of Classification Search
CPC .......... A61L 2/28; C07H 21/04; C07K 14/78; C12Q 1/6844; C12Q 2563/185; G01N 31/226; G01N 33/025
See application file for complete search history.

(56) References Cited

U.S. PATENT DOCUMENTS 4,593,360 A 6/1986 Cocks
6,312,911 B1 11/2001 Bancroft et al.
(Continued)

FOREIGN PATENT DOCUMENTS

CN 101379188 A 3/2009
CN 104024426 A 9/2014
(Continued)

OTHER PUBLICATIONS

Oxford Gene Technology (2011) "DNA Storage and Quality", downloaded from https://www.ogt.com/resources/literature/403_dna_storage_and_quality on Oct. 30, 2018.*
(Continued)

*Primary Examiner* — Jeremy C Flinders
(74) *Attorney, Agent, or Firm* — Haynes and Boone, LLP

(57) ABSTRACT

A pathogen surrogate, formed by a DNA tag or bar code and a carrier, is described for use in the validation and verification of sanitation, such as in food processing operations and for wash water systems for fresh produce. The carrier material is selected so that the pathogen surrogate mimics the behavior of a pathogen when subjected to a sanitation operation. One or more surrogates can be introduced in to an environment, which is then subjected to sanitation process, followed by a detection process using the DNA tag of the surrogate.

20 Claims, 3 Drawing Sheets

(51) Int. Cl.
*G01N 33/02* (2006.01)
*C07H 21/04* (2006.01)
*C12Q 1/6844* (2018.01)
*C07K 14/78* (2006.01)

(52) U.S. Cl.
CPC ......... *G01N 33/025* (2013.01); *C12Q 1/6844* (2013.01); *C12Q 2563/185* (2013.01)

(56) References Cited

U.S. PATENT DOCUMENTS

| | | | |
|---|---|---|---|
| 8,293,535 B2 | 10/2012 | Farquar et al. | |
| 2002/0129523 A1 | 9/2002 | Hunt | |
| 2004/0166520 A1 | 8/2004 | Connolly | |
| 2006/0037222 A1 | 2/2006 | Hunt et al. | |
| 2010/0261193 A1 | 10/2010 | Webster et al. | |
| 2011/0177539 A1* | 7/2011 | Sutton | C12Q 1/485 435/8 |
| 2012/0112883 A1 | 5/2012 | Wallace et al. | |
| 2013/0052751 A1 | 2/2013 | Farquar et al. | |
| 2013/0122807 A1 | 5/2013 | Tenarvitz et al. | |
| 2014/0057276 A1 | 2/2014 | Farquar et al. | |
| 2014/0220576 A1 | 8/2014 | Macula | |
| 2014/0255984 A1 | 9/2014 | Sharpin | |
| 2014/0272097 A1 | 9/2014 | Jung et al. | |
| 2014/0340423 A1 | 11/2014 | Taylor et al. | |
| 2015/0322426 A1 | 11/2015 | Zografos et al. | |
| 2015/0361490 A1 | 12/2015 | Farquar et al. | |
| 2016/0102335 A1 | 4/2016 | Franciskovich et al. | |
| 2016/0171179 A1 | 6/2016 | Donofrio et al. | |
| 2016/0188943 A1 | 6/2016 | Franz | |
| 2017/0038353 A1 | 2/2017 | Zografos et al. | |
| 2017/0197002 A1 | 7/2017 | Dobrinsky et al. | |
| 2017/0322701 A1 | 11/2017 | Bowman et al. | |
| 2017/0333859 A1 | 11/2017 | Lind | |
| 2018/0252738 A1 | 9/2018 | Denney | |

FOREIGN PATENT DOCUMENTS

| | | |
|---|---|---|
| CN | 104131008 A | 11/2014 |
| CN | 104513863 A | 4/2015 |
| WO | 2008137831 A1 | 11/2008 |
| WO | 2011163296 A2 | 12/2011 |
| WO | 2012037876 A1 | 3/2012 |
| WO | 2014164958 A1 | 10/2014 |

OTHER PUBLICATIONS

Busta et al., "The Use of Indicators and Surrogate Microorganisms for the Evaluation of Pathogens in Fresh and Fresh-Cut Produce," Comprehensive Reviews in Food Science and Food Safety, 2(s1), Jan. 2003, pp. 179-185.

Danyluk et al., "Process Validation: Selection and Use of Surrogates," University of Florida Institute of Food and Argicultural Sciences, presentation dated Apr. 2014, 19 pages.

Farquar, "DNATrax (DNA Tagged Reagents for Aerosol eXperiments)," Lawrence Livermore National Laboratory, presentation LLNL-PRES-642415, Aug. 2013, retrieved from the internet at <http://web.archive.org/web/20160226230017/https://ipo.llnl.gov/technologies/individual-tech-discovery&p=DNATrax>, 6 pages.

Ma et al., "Development of Thermal Surrogate Microorganisms in Ground Beef for In-Plant Critical Control Point Validation Studies," Journal of Food Protection, 70(4), Apr. 2007, pp. 952-957.

Niebuhr et al., "Evaluation of non-pathogenic surrogate bacteria as process validation indicators for *Salmonella* enteric for selected antimicrobial treatments, cold storage and fermentation in meat," Journal of Food Protection, 71(4), Apr. 2008, pp. 714-718.

Sinclair et al., "A Criteria for Selection of Surrogates Used to Study the Fate and Control of Pathogens in the Environment," Applied and Environmental Microbiology, 78(6), published online Jan. 13, 2012, published in print Mar. 2012, pp. 1969-1977.

Yeater et al., "Effectiveness of Sanitzing Products on Controlling Selected Pathogen Surrogates on Retail Deli Slicers," Journal of Food Protection, 78(4), Apr. 2015, pp. 707-715.

Hou et al., "Rapid bioparticle concentration and detection by combining a discharge driven vortex with surface enhanced Raman scattering," Biomicrofluids 1.014106:1-13, Feb. 16, 2007.

International Search Report and Written Opinion dated Sep. 8, 2016, International Patent Application No. PCT/US2016/038083, filed Jun. 17, 2016.

Puddu et al., "Magnetically Recoverable, Thermostable, Hydrophobic DNA/Silica Encapsulates and Their Application as Invisible Oil Tags," ACS Nano 8(3):2677-2685, Feb. 25, 2014.

Andrews, "DNA Spray-On Technology Could Revolutionize Food Traceability," Food Safety News, http://www.foodsafetynews.com/2014/11/dna-laced-spray-technology-could-revolutionize-food-traceability/#.W1kRNNVKjRY, Nov. 17, 2014, 2 pages.

Bystrykh, "Generalized DNA Barcode Design Based on Hamming Codes," PLOS ONE 7(5):e36852, May 17, 2012, 8 pages.

Naaum, "Novel Methods of Species and Product Authenticity and Traceability Testing Using DNA Analysis for Food and Agricultural Applications," Doctoral Dissertation, Department of Integrative Biology University of Guelph, Apr. 2014, 144 pages.

International Search Report and Written Opinion, dated Mar. 15, 2019, International Patent Applicaton No. PCT/US19/13069, filed Jan. 10, 2019, 13 pages.

Harding et al., "Unique DNA-barcoded aerosol test particles for studying aerosol transport," Aerosol Science and Technology 50(5):429-435, Mar. 22, 2016.

International Search Report and Written Opinion dated Aug. 8, 2019, International Patent Application No. PCT/US2019/029002, filed Apr. 24, 2019, 8 pages.

Sharma et al., "Hydrological Tracers Using Nanobiotechnology: Proof of Concept," Environmental Science and Technology, 46(16):8928-8936, Aug. 21, 2012.

* cited by examiner

PATHOGEN SURROGATES BASED ON ENCAPSULATED TAGGED DNA FOR VERIFICATION OF SANITATION AND WASH WATER SYSTEMS FOR FRESH PRODUCE

CROSS-REFERENCE TO RELATED APPLICATIONS

This application claims priority from U.S. Provisional Application No. 62/200,456 filed on Aug. 3, 2015, which is hereby incorporated in its entirety by this reference.

BACKGROUND OF THE INVENTION

The following disclosure relates generally to the validation and verification of sanitation, disinfection and wash processes and, more specifically, to the use of tagged DNA for such verification.

Microorganisms are biological entities that can be beneficial or hazardous to humans and to the food manufacturing industry. Bacteria represent the largest group of microorganisms. Most bacteria are harmless; in fact, some provide benefits to humans by protecting the skin and nasal passages and also aid in the digestion process. Some also benefit the food industry, when they are used for production of cultured items, such cheese, yogurt, and fermented sausage. However, they can pose a threat to humans and to the industry when they result in foodborne illness and food spoilage. Microbiological contamination of food may result in product spoilage, reduction in shelf life, or foodborne illness.

The time used in cleaning a food plant is time away from production. Yet, it is production that is the purpose of a food plant, provided production is wholesome, unadulterated, and of a quality level that people will continue to buy the finished product. Without a sanitation process in a food plant, it is likely that none of these expectations will be met. Sanitation is basic to food safety and quality. It is a vital segment of an integrated food safety system with strong links to regulatory compliance, quality, Hazard analysis and critical control points (HACCP), (Good manufacturing practices) GMPs, and pest control. The process of sanitation has many facets that make it vital in a food plant, not the least of which is that it allows food companies to meet regulatory standards. Of course, the primary function is to remove contaminating soils, prevent film buildup, and prepare food contact surfaces for production. It is also necessary to prevent insect and rodent infestation and harborage by removing sources of attraction and nutrition. Effective sanitation also plays an important role in preventing allergen cross-contamination and foreign material inclusions. The benefits of effective sanitation are production of safe product, improved product shelf life, and reduction of off-flavor, odor, and color. To an extent, it will also prevent equipment deterioration and increase production efficiency. Finally, it can be a source of pride and morale to employees who prefer to work in a location that is clean.

Contamination can also occur in wash water systems used in fresh produce processing. Food agriculture occurs mostly outdoors, so the food products are susceptible to contamination from the soil in which it is grown, various arthropods that co-inhabit the environment, and excreta from birds and other animals. Thus, most fruits, vegetables, and nuts sold as fresh produce in the U.S. are washed by the packer/shipper prior to distribution. This washing is effective at removal of gross contamination, which may be associated with fungi and bacteria that can cause disease or accelerate spoilage. However, microbiological contamination is comparatively tenacious and may not be adequately reduced by washing under conditions that preserve the product. In terms of HACCP, washing is not considered a kill step. In fact, washing produce creates a risk of inadvertent cross-contamination, as the contaminant breaks down and spreads microorganisms throughout the wash.

In order to reduce the likelihood of microbial contamination of produce, wash water (and wash water additives) should not only remove attached microbes from the surface of the produce, but also prevent microbial deposition from the wash water to the produce. Validation of these methods requires experiments using target organisms. However, intentional contamination of industrial food handling equipment with pathogens and spoilage organisms is counterproductive. Non-pathogenic bacteria, which have similar responses to specific food processes as the pathogenic bacteria, have been developed for food processors to validate a process in-plant, without the use of actual pathogens. However, the industry is resisting the use of live bacteria in food processing plants, whether they are considered pathogenic or not. This is partly because of experiences with organisms which were considered non-pathogenic but caused reported illnesses, and partly because DNA fragments from these organisms may be detected during routine microbial testing and result in false positives with highly detrimental economic effects.

SUMMARY

In a first set of aspects, a product includes a DNA bar code and a non-toxic pathogen surrogate carrier. The DNA bar code is combined with the surrogate carrier to form a pathogen surrogate, where the pathogen surrogate is degradable under a sanitation process.

In another set of aspects, a method of providing a pathogen surrogate includes receiving a carrier formed of a non-toxic substance and combining a DNA bar code with the carrier to form a pathogen surrogate. A benchmarking operation is performed to determine whether pathogen surrogate behaves similarly to a first pathogen when subjected to a sanitation operation.

In a further set of aspects, a method of testing the efficacy of a sanitation process includes introducing a first pathogen surrogate formed of a DNA bar code encapsulated in a non-toxic pathogen surrogate carrier. A sanitation operation is subsequently performed. A detection operation determines the amount of the first pathogen surrogate present after performing the sanitation operation.

All patents, patent applications, articles, books, specifications, other publications, documents and things referenced herein are hereby incorporated herein by this reference in their entirety for all purposes. To the extent of any inconsistency or conflict in the definition or use of a term between any of the incorporated publications, documents or things and the text of the present document, the definition or use of the term in the present document shall prevail.

DETAILED DESCRIPTION OF EXEMPLARY EMBODIMENTS

The DNATrax technology described herein is already used in aerosol formulations for simulation of bio-threat microparticles in modeling terrorist attacks, and for tracking and quantifying particulate migration. See for example, U.S. Pat. No. 8,293,535 and U.S. Application 2014/0057276 on the formation of DNA tagged microparticles in this context. Related U.S. Application 2014/0272097 discloses DNA marking of items for authenticating the items, while U.S. patent application Ser. No. 14/599,315 extends the use of such materials to the problem of tracing the origin of food products. However, none of these functions relate to the use of such DNA bar code or tag ("bar code" and "tag" are used interchangeably herein) to the verification of sanitation and wash water systems for fresh produce. Although the following discussion will be mainly in the context of food processing, it is also relevant in other application such as disinfection and sanitation of healthcare facilities, medical devices, aerospace missions, and other applications.

In the sanitation context, the particle properties can be adjusted to simulate the behavior of living organisms (often, although not necessarily, pathogenic) under specific conditions, such as pH, temperature, etc. Chemical reactions between the carrier materials and the sanitizers promote the destruction of the particles at rates that are either similar or correlate to those of the target pathogens. Further, the surface properties of the particles can be adjusted to adhere to processing or product surfaces in a way that is similar to that of the target organisms. Some examples of pathogens where these techniques could be applied in the food processing context and more generally, such as in a healthcare settings, include salmonella, methicillin-resistant Staphylococcus aureus (MRSA), and Clostridium difficile, tuberculosis (MTB, TB), hepatitis B, and human immunodeficiency virus (HIV), among others.

Sanitation Validation and Verification

No sanitation system is complete without proof of effectiveness. For industries concerned with safe and reproducible production, the initial rigorous proof of effectiveness for a new process is called validation. A proof for effectiveness of the same process with slightly different equipment (e.g., after maintenance) or a slightly different product (e.g., a new lot of raw material) is called verification. Verification is typically performed more frequently than validation and is typically somewhat less rigorous.

Validation and verification may be done in several ways, from simple and relatively inexpensive to slightly more expensive and complex. The least expensive and easiest to implement is visual or organoleptic examination of the post-sanitation and pre-operation environment. Organoleptic pre-op inspection is normally required as part of the plant's SOP, and there is no regulatory requirement to incorporate other investigative tools. However, added investigative tools and documentation provide extra insight into the thoroughness of the sanitation process. Adenosine triphosphate (ATP) or bioluminescence measurement is an extremely effective, relatively inexpensive tool that many food manufacturers employ for rapid verification feedback about sanitation. Microbiological testing is a tool used by many companies as a means of both verification and validation of sanitation.

Organoleptic testing involves direct sight, smell, and touch. This is typically performed as verification during pre-op inspection, following the sanitation process. It involves inspection of the equipment, obviously using the sense of sight to look for any indications of food material left on equipment, such as grease, dough, or produce, depending on the products being handled in the plant. The sense of smell may identify hidden material and is especially sensitive for detection of putrescence. Touch can detect thin films that are slippery, sticky, or rough in texture.

Rapid microbial detection is becoming increasingly essential to many companies in the pharmaceutical, clinical, and in the food and beverage areas. Faster microbiological methods are required to contribute to better control of raw materials as well as finished products. Rapid methods can also provide better reaction time throughout the manufacturing process. Rapid technologies provide companies with cost savings and speed up product releases.

Despite clear disadvantages, traditional microbial detection methods are still widely used. Current methods require incubation of products in liquid or solid culture media for routinely 2 to 7 days before getting the contamination result. This necessary, long incubation time is mainly due to the fact that stressed microorganisms found in complex matrices require several days to grow to visible colonies to be detected. Moreover, this incubation period can be increased up to 14 days in specific applications like sterility testing for the release of pharmaceutical compounds. This delay can cause two significant problems. One is that fresh foods have a limited shelf life, not much longer than the 7 to 14 days required for culture testing. So these products must be shipped prior to test results. The other problem is that, in the case of an outbreak of foodborne disease, victims get sick and die during those 7 to 14 days before the product is confirmed to be contaminated and a recall is accomplished.

Although these techniques have advantages including technical robustness, low skill and training requirements, the use of inexpensive materials and their acceptability to the regulatory authorities, the major drawback is the length of time required to get microbiological results. Thus, in light of the growing demand for rapid detection methods, various alternative technologies have been developed. In the field of rapid micro-organisms detection, ATP bioluminescence based on luciferin/luciferase reaction has garnered great interest.

Adenosine triphosphate (ATP) is found in all living organisms and is an excellent marker for viability and cellular contamination. Rapid detection of ATP through ATP-luminescence technology is therefore a method of choice to replace traditional methods and significantly shortens the time to detection. However, ATP has a number of disadvantages, including: It does not easily distinguish between ATP from microorganisms, animals, and plants; luminescence from product can generate spurious ATP bioluminescence readings; the presence of detergents, sanitizers, or other chemicals also can affect the readings; and it is not sensitive for spore detection, where ATP is very low.

Use of Surrogates in Sanitation

One of the practical limitations of process validation is that the actual pathogens cannot be taken in to a food-processing establishment to verify a specific process. While laboratory research can be used as a reference point, it is not a true substitute for actual, in-plant process validation. The availability of non-pathogenic bacteria, which have similar responses to specific food processes as the pathogenic bacteria, offers the food processor the ability to validate a process in-plant, without the use of the actual pathogens. For example, coliforms have been used as process indicators for pasteurization in the dairy industry.

The term surrogate is used to indicate a substitute for an item of interest. In the context of environmental microbiology and health risk assessment, a surrogate is defined as an organism, particle, or substance to study the fate of a pathogen in a specific environment. Surrogates may be released into the environment to evaluate decontamination or disinfection achieved within a food processing plant. In this case, the surrogate should not damage or contaminate the equipment or processes, or at least the equipment can be easily decontaminated. Surrogates should be avoided if they could cause undesirable biofilm formation, taste, odor, physicochemical changes, or an opportunistic infection. In some cases, the surrogate should not have a long-term persistence in the environment. It should be predictable, easily detected, and decontaminated without jeopardizing industrial equipment or natural environments. Both pathogenic and non-pathogenic organisms have been used as surrogates for a variety of purposes including studies on survival (under environmental conditions and during disinfection), transport as well as for methods development and as "indicators" of certain conditions.

A useful surrogate must display behavior (in the product/process of interest) similar to pathogens, spoilage bacteria and fungi, or other target organisms. This includes attachment and growth under conditions of inadequate sanitization, and complete neutralization under sanitization conditions that remove the target. This implies that the surrogate is changed by the process. For example, a cleaning process may either render target microbes unable to attach, or kill them in place. Likewise, an effective surrogate may be converted into an unattached state by effective sanitization, or simply converted into an undetectable state.

A surrogate preferably also would have the following characteristics:
  Safe (non-pathogenic, not hazardous to equipment or operating personnel);
  Can be detected rapidly to allow for additional sanitation steps to be taken, if necessary, without significant incremental plant downtime;
  Inexpensive;
  Easy to store, prepare, apply, sample, and detect/enumerate;
  Easy to differentiate from residual product or background microflora; and
  Will not establish as a "spoilage" organism in the processing facility.

Encapsulated DNA Sequences as Surrogates

Figure 1:
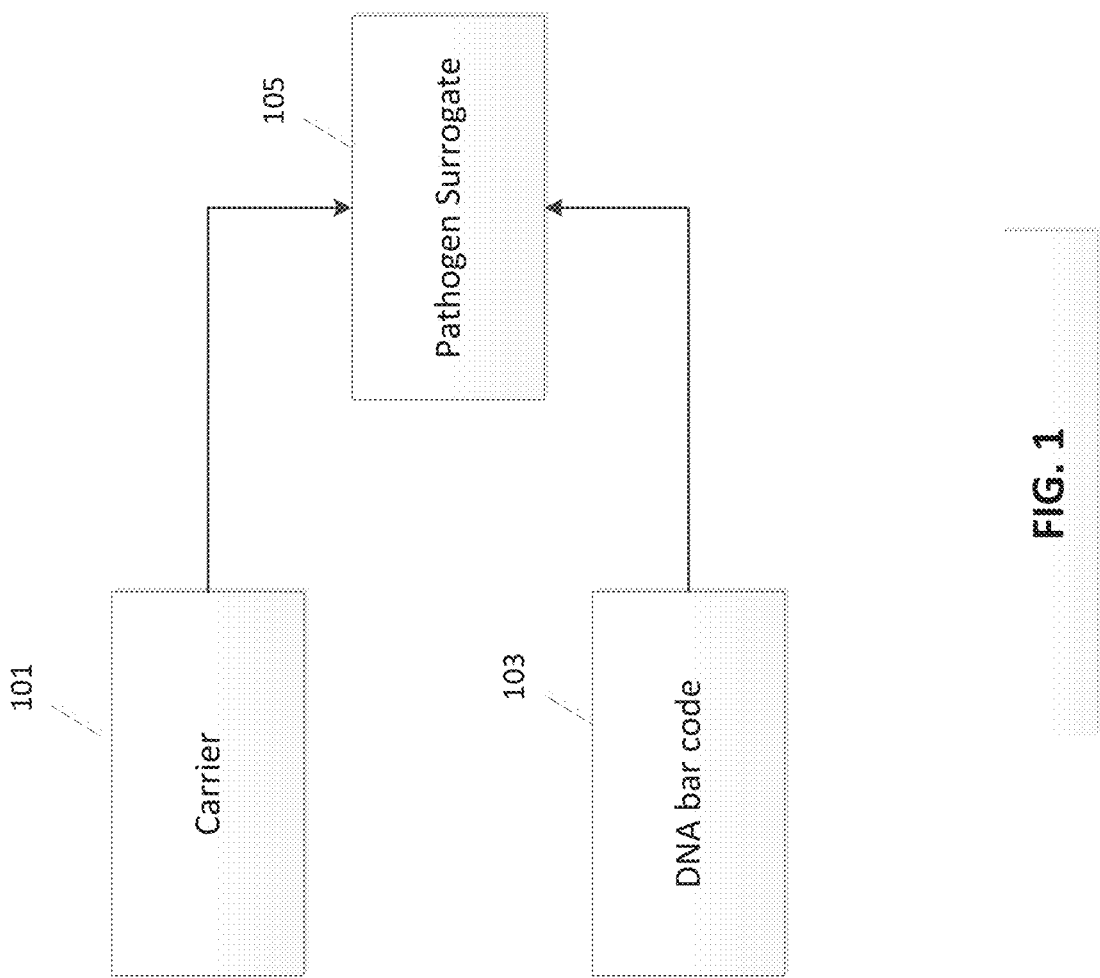
FIG. 1 illustrates a pathogen surrogate formed of DNA bar code and a carrier material.
Figure 2:
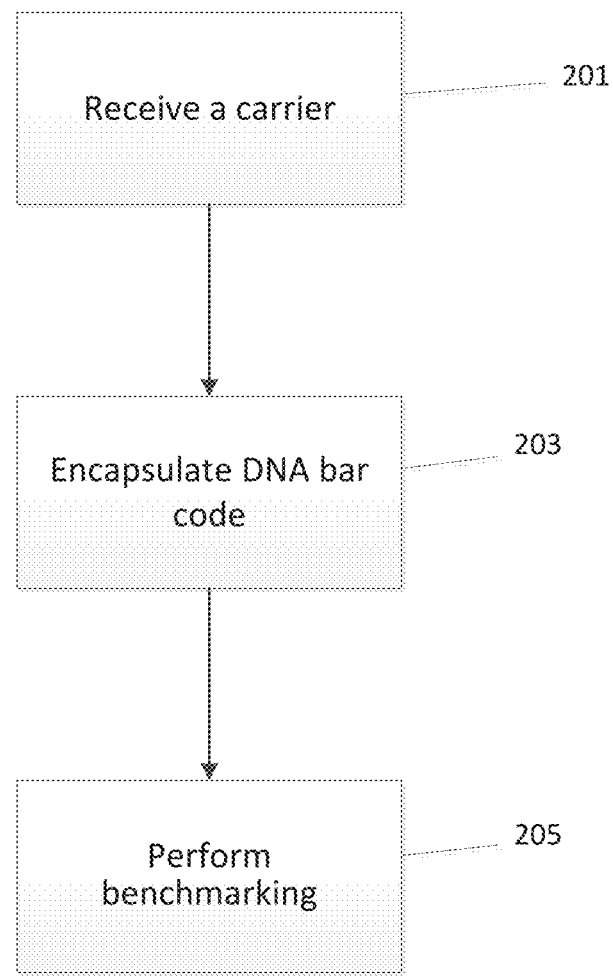
FIG. 2 presents a method of providing a pathogen surrogate.

Advances in bio-engineering have produced materials that enable the development of an efficient, effective and low cost food pathogen surrogate system. These surrogates can be formed through the use of trigger DNA, as a DNA bar code or as a simple tag encapsulated in the carrier. FIG. 1 is a schematic illustration of a pathogen surrogate 105 formed by combining a DNA bar code 103 and a carrier material 101. FIG. 2 outlines a method for determining the effectiveness of the surrogate, where the carrier is received at 201, combined (encapsulated, absorbed, and/or adsorbed) with the DNA tag at 203, and the benchmarking of the surrogate is performed at 205. In one possible embodiment, the trigger DNA consists of a substance comprising around 90-150 DNA base pairs of natural or synthetic DNA. Maltodextrin, salt, starch or many other food grade materials may be used as carriers. Additionally, non-water-soluble food grade polymers, proteins, membrane lipids, etc. can be used as carriers. The particle is a safe, size-selectable surrogate containing DNA that is not biologically active, but nonetheless contains information chemically encoded by the specific base sequence.

Measurement of DNA molecules is commonly performed through processes that specifically amplify the copy number of only those molecules bearing a specific target base sequence. Such processes include thermal cycling (polymerase chain reaction, aka PCR) and isothermal technologies (including loop-mediated isothermal amplification, aka LAMP). These methods amplify, detect, identify, and quantitate the target molecule. For DNA molecules>60 bases in length these methods may be used to simultaneously measure many targets using a single reaction. And such multiplexing can take advantage of both differences in the target base sequence, as well as lengths of the target molecules. Preparation of such sets of related/similar target sequences is straightforward for synthetic DNA. For DNA isolated from natural sources the sequence could be varied through standard molecular biology techniques.

Quantitation may be performed concomitant with these amplification technologies, e.g., through the use of quantitative PCR or assimilating probe LAMP. Otherwise the detection and quantitation may be performed using complementary technologies, such as surface enhanced Raman spectrometry (SERS) or surface plasmon resonance (SPR).

Encapsulated short DNA sequences offer the opportunity to develop a set of surrogate particles that can behave very similarly to a corresponding set of target pathogens, which may be found in a food processing plant. DNA sequences containing 100 or less base pairs are safe and have been approved by the FDA as Generally Recognized As Safe (GRAS) food additives. The surrogate particles can be produced in large quantities at relatively low cost. By varying the carrier material and formulation details, the surrogates' physico-chemical properties may be adjusted over a wide range of particle size, hydrophobicity, porosity, solubility, etc. Thus the behavior of the surrogates, including adherence to the product and processing equipment, can be tuned to match those of specific pathogens. The surrogates' resistance to various disinfection and sanitation agents and methods can be further adjusted by inclusion of UV inhibitors, anti-oxidants or other chemical modifiers in the carrier material.

The surrogates may be combined with antibacterial components to which they are resistant to provide a combination of sanitation and sanitation verification in a combined application. In certain applications, the addition of isotopic tags, SERS-enhanced particles, or fluorescent materials, such as quantum dots or nano-dots to the surrogates may enable faster detection methods. The surrogates' stability over time may be adjusted by inclusion of oxidizers in the carrier material. By varying the surrogates' carrying material, their stability under varying temperature, humidity, and pH conditions may be adjusted. The surrogates may be introduced to the process via a variety of methods, as solid powders (sols), aerosols or liquid sprays.

Different target organisms may behave quite differently in any given process, and the same target organism may behave differently in slightly different processes. Thus surrogates will comprise various formulations of the DNA tracer molecules. For each target organism-process pair a panel of surrogates should be studied. Under test conditions, the surrogates and actual target organisms should be introduced together, and then sampled and measured together, both before and after sanitation. Some surrogate formulations will prove more labile than the target, and some will prove less labile. Judicious choice of surrogate formulations, measurement methods, and quantitative decision points should allow selection of a proper surrogate or set of surrogates for accurate modeling of target behavior.

For benchmarking purposes, the maximum likelihood method is useful to assess the performance of the chosen sanitation method. After this, a covariance analysis can be used to compare the pathogens' and the surrogates' survival rates and ensure that the surrogate and the pathogen exhibit the same behavior.

Sanitation Validation/Verification

Figure 3:
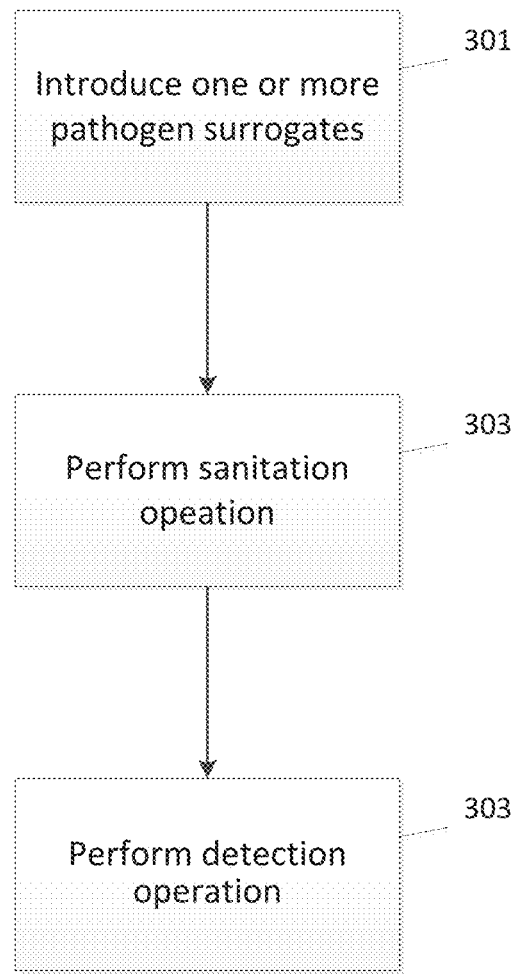
FIG. 3 illustrates the use of pathogen surrogates in a sanitation process.

The validation/verification process can include surrogate selection, preparation, and introduction, the sanitation process, and quantitation of the surrogate. FIG. 3 outlines the procedure: at 301 one or more surrogates are introduced, with the sanitation process following at 303, after which a detection operation is performed at 305. As for surrogate preparation, the surrogate used for the validation is prepared in the same way as it was prepared during the benchmarking procedures establishing its correlation with the target organisms.

The surrogate can be introduced into the plant in a way that does not alter the normal condition of the environment. The surrogate may be introduced in a variety for methods, for example as an aerosol covering large areas of the plant, as a suspension in a liquid spray for a more targeted application, or on coupons that have been inoculated with known quantities of the surrogate and placed at specific locations in the plant (as for example areas known to be challenging for sanitization). This list is not exhaustive as other methods specific to the environment and sanitation method may be employed. Because of the very large number of unique DNA barcodes available, differentiated surrogates of the same pathogen may be released at different locations in a plant to study the transport of the pathogen, for example, from the raw materials area to the shipping area. After the surrogate is introduced in the plant the sanitation process is performed per normal operating procedure.

Following exposure of the surrogates to the sanitation process, the surviving surrogates must be recovered and enumerated, as either (a) count reduction method where the number of surviving surrogates is estimated and the log reduction can be calculated by simply subtracting the log of the number of survivors from the log of the initial number of surrogates or (b) end point technique where multiple samples are collected and the log reduction can be calculated based on the number of units that test positive for surviving surrogates.

Once the log reduction for the surrogate is calculated it can be converted to the theoretical log reduction of the target pathogen(s) using the pre-established correlations between surrogate and pathogen. It can then be determined whether the control process meets the accepted criteria and the desired safety objective, thus achieving validation.

One application for which these surrogates are particularly suitable is simulation of microbial biofilm. In naturally occurring biofilms microorganisms form colonies that adhere to solid surfaces through molecular and physico-chemical mechanisms that are currently poorly understood and extremely difficult to model. Organisms in biofilms are unusually resistant to all methods of sanitization. To mimic biofilms surrogates can be formulated in thick, adherent preparations of edible/GRAS gels and gums. These gels may be prepared from agar agar, carrageenan, gellan, gelatin, latex, glycerol ester of wood rosin, or various other starches, pectins, and proteins, to name a few possibilities.

Other Applications

These techniques can be extended to a number of other applications, as validation is required in many settings other than food processing. For example, sanitation and validation are performed in healthcare settings including room surfaces, garments and medical devices; in "clean" manufacturing; and on spacecraft prior to launch. The surrogate method described here is similarly applicable to all applications.

Water Wash Systems for Fresh Produce

As a salient example food safe pathogen surrogates with a DNA tag or bar code can also be used for the validation and verification of wash water systems such as those used in fresh produce processing. As noted above, food agriculture occurs mostly outdoors, so the food products are susceptible to contamination from the soil in which it is grown, various arthropods that co-inhabit the environment, and excreta from birds and other animals. Thus, most fruits, vegetables, and nuts sold as fresh produce in the U.S. are washed by the packer/shipper prior to distribution. This washing is effective at removal of cross-contamination, which may be associated with fungi and bacteria that can cause disease or accelerate spoilage; however, microbiological contamination is comparatively tenacious and may not be adequately reduced by washing under conditions that preserve the product. In terms of HACCP, washing is not considered a kill step. In fact, washing produce creates a risk of inadvertent cross-contamination, as the gross contamination breaks down and spreads microorganisms throughout the wash.

Thus, other than rinsing off perceptible filth, the major function of produce wash water (and wash water additives) is not to remove attached microbes from the surface of the produce, but to prevent microbial deposition from the wash water. Although many additives have been tested, the emerging paradigm suggests that chlorine is effective to keep the clean produce clean, while preserving quality. Too much chlorine can rapidly damage produce and/or leave an unpleasant lingering odor. Too little chlorine risks contamination of clean material by microbes released into the wash water. Thus, modern produce washing facilities often incorporate automation to maintain an optimum concentration of active chlorine, as it is continuously consumed by the bio-organic load of produce and filth. These systems sometimes also manage additional additives, such as citric acid to maintain pH below 6.5.

In addition to chlorine and pH, other variables affect wash efficiency. These include temperature, contact time, and agitation, as well as the variable survival and adherence of different contaminating micro-organisms. Appropriate washing conditions are related to characteristics of the produce. For example, leaf lettuce must be gently floated in cold water to prevent damage, while potatoes are better cleaned with vigorous mechanical friction. Practically, these conditions are already established through industry's deep experience with washing of produce. However, validation of these methods for prevention of microbial cross-contamination has not been performed. In theory, reproducible wash conditions may be validated to demonstrate effectiveness, and automation can generate a verifiably safe and wholesome fresh product.

One of the practical limitations of wash systems validation and verification is that actual pathogens cannot be taken in to a food-processing establishment to verify a specific process. While laboratory research can be used as a reference point, it is not a true substitute for actual, in situ validation. The availability of non-pathogenic bacteria, referred to as surrogates, which have similar responses to specific food processes as the pathogenic bacteria, allows food processors to validate a process in-plant, without the use of actual pathogens. As mentioned earlier, however, the industry is resisting the use of live bacteria surrogates in food processing plants, whether they are considered pathogenic or not, in part because of past experiences with organisms that were considered non-pathogenic but caused reported illnesses, and in part because DNA fragments from these organisms may be detected during routine culture-independent microbial testing and result in presumptive positives with highly detrimental economic effects.

As indicated above, produce washing faces two primary challenges. One problem is that contaminants may adhere to the produce or processing equipment in the form of recalcitrant biofilms that respond in a limited fashion to aggressive washing. The other problem is that any microorganisms that are effectively washed off from a spot contamination may subsequently adhere to clean produce, spreading a small concentrated contamination throughout a large number of product servings. The surrogates described may be used to address both of these challenges.

To address the first challenge, the surrogate can be formulated in a gel or gum that mimics the behavior of a biofilm in the wash system. This material may be applied to the surface of the processing equipment, to a selected piece of produce, or to a proxy (such as a tennis ball in an apple operation). Different surfaces may require different respective formulations, which may be achieved through adjusting the physical and chemical parameters of the surrogate particle formulation. For example, the waxy cuticle of leafy produce may adhere well to hydrophobic surrogate formulations, which may be produced through incorporation of lipids, while steel may adhere better to particles providing an anionic surface, which may be produced through incorporation of organic acids or other chelators.

Properly tuned through selection and adjustment of the specific formulation, such a surrogate will partly wash away, but partly remain stuck to the surface. Thus, after the wash process is completed the originally contaminated item can be retrieved, sampled, and tested to measure the remaining DNA tracer signal. An effective wash process might fully remove the surrogate, which mimics removal of adherent micro-organism biofilm. Alternatively, an effective wash might simply render the surrogate undetectable, mimicking killing of the microorganisms in the biofilm.

These two possible effects are not necessarily operationally equivalent, and monitoring the wash water for the presence of micro-organisms and surrogates can distinguish between them. If the micro-organisms and surrogates are eluted from the surface intact, then they may redeposit on clean surfaces. This is especially problematic if a pathogen re-deposits onto the surface of produce. As indicated above, this is the second challenge faced by produce wash methods. This second challenge (re-deposition) can be separated from the effect of the first challenge (contaminant removal) by adding the surrogate to the wash water, rather than a washed solid surface.

After the surrogate is introduced in the system, the wash process can be performed following normal operating procedure. Under effective wash conditions, in which microbes cannot attach to produce, a surrogate similarly will not stick well to the produce. To some extent, this may occur via destruction of the target organisms and surrogate material, via reaction with chlorine and other additives. Alternatively, the surrogate and microbes may both simply remain in the water, but not attach to the produce. This may occur through changes in the surface of the produce, the microbes, and/or the surrogate. On the other hand, wash conditions that are too mild can allow microbes and surrogate to bind to the produce. Then if a surrogate is detected on produce sampled after the wash process, it will serve as indication that the process can result in cross contamination and therefore failed to perform its intended function. Detected within minutes, the DNA tag will allow for accurate validation and verification that is faster and less expensive than other methods.

Surrogate Production

The DNA sequences of the surrogates are produced using bioinformatics, to prevent any false positives from other sources. They may be based on theoretical molecules, naturally-occurring DNA, or based on an existing library of DNA sequences developed for biodefense and food traceability applications. The DNA portion of the surrogate may be produced chemically, synthetically using biotechnology (either cell-free molecular biology or cloning into an expression bacteria or yeast), or via isolation/purification from natural sources. The robustness of the DNA carrier material defines the resistance of the surrogate to the sanitizing agent.

For example, surrogate that is easy to destroy via sanitization can be developed, based on a DNA tagged biosimulant for aerosol transport studies. The formulation can be a maltodextrin carrier and be water-soluble. The solubility of the material makes the DNA readily available to any oxidative sanitizer, such as active chlorine, if the material is in a water environment. This allows for a very basic but significant check for cleaning procedures (i.e., was any cleaning conducted with sanitizer?).

A PLGA-based carrier can also be used. PLGAs are FDA approved biodegradable copolymers of poly(lactic-co-glycolic acid) commonly used for drug delivery. PLGA decomposes through hydrolysis, and this process is accelerated at elevated pH and oxidative conditions. PLGA hydrolysis rates are also dependent on the ratio of the lactic and glycolic acid ratios. This dependence will allow the process to fine-tune the degradation rates to match a target pathogen. The surface of PLGA is relatively hydrophobic and may associate with surfaces non-specifically. PLGA also bears pendant carboxylic acid groups, which may be chemically modified to introduce a relatively low density of functional ligands.

In other embodiments, a surrogate can be produced from a gelatin-based carrier. Gelatin has many unique properties, most notably very low solubility in cold water and high solubility in hot water. Because it is a protein, gelatin provides a particle surface bearing primary amine and carboxyl chemical moieties, which are easily modified via controllable chemical reactions, producing a relatively high density of ligands. Other temperature-dependent surrogates may also be used. Other examples of surrogate carrier can include: carrageenan, carnauba, silica, water-soluble carbohydrate, flour, albumin, casein, a particle bearing a core of a functionally ferromagnetic material, or carrier using fixed (killed) cells of a formerly living microorganism.

A two-step mechanism to deactivate the DNA of the surrogates can be used, wherein step 1 will induce a chemical change to the carrier, causing the release of a DNA deactivating compound in step 2.

Surrogate Benchmarking

In many applications it is useful that a surrogate actually gives a slight background when no microbes are recovered. In one embodiment, a mixture of three DNA tagged surrogates, each formulated for different stability, can be used. One formulation of the surrogates can use a carrier or formulation selected to exhibit overly robust attachment to the produce matrix. Under wash conditions that are validated to prevent microbial attachment, this surrogate will detach from the spiked produce, survive the wash water, attach to unspiked produce in the wash, and exhibit strong recovery from the washed produce. This component will serve as a positive control for industrial validation.

A different surrogate can be formulated as the negative control. This component will be developed with a labile formulation, such as a carbohydrate formulation, which will exhibit no attachment when subjected to a mild pure water rinse, while target microbes remain strongly attached. Inadvertent recovery of this surrogate component will indicate problems with sample handling, including inoculum cross-contamination or a skipped wash step.

A third component can be tuned for low but measurable attachment and recovery. For example, under validated wash conditions it will return a background of $10^2$ to $10^3$ copies of surrogate (and zero microbes). A result of more than $10^4$ copies of the surrogate thus suggests wash failure, i.e., non-verification. Higher numbers of surrogate recovery will correlate with higher possibility and higher most probably number of microbes (more serious failure of the wash step), the numerical relationship between surrogate and microbe counts may not be linear.

In the determination of different formulations, unwashed spiked produce can provide quantitation of the inoculum (microbes and surrogate), as a positive control, and unspiked samples can provide a negative control. Additionally, residual wash water can be tested for microbes and surrogate as internal controls. The ramifications of a false negative test for sanitation are quite serious. Thus, it is often preferable to minimize the possibility of false negatives, at the expense of an increased chance for false positives. The system can be designed and developed to yield a signal that is above background in the presence of effective washing. An unusually low signal in a sample (between, say, zero and $10^2$ copies of surrogate) might therefore result from unusually stringent washing, while a low result in the positive control will generally indicate a failure of the surrogate system. False positives, on the other hand, are minimized by including a negative control in addition to our low-level surrogate.

Other detection devices can be based on high-performance biosensor arrays using a CMOS (complementary metal-oxide-semiconductor) manufacturing processes. The devices based on this technology are generally referred to as CMOS biochips and can identify multiple targets, including nucleic acids (DNA or RNA), peptides, or metabolites, in a massively parallel fashion ($10^2$ to $10^8$ biosensors per biochip). CMOS biochips are highly integrated and include not only the molecular detection elements, but also all the analog sensor interface, data converter, and digital signal processing (DSP) components. This integration means that they do not require a bulky reader, scanner, delicate optics, or sophisticated microfluidics like conventional diagnostic instruments today. A CMOS biochip is a bio-analysis instrument-on-a-chip.

Conclusion

Although the various aspects of the present invention have been described with respect to certain preferred embodiments, it is understood that the invention is entitled to protection within the full scope of the appended claims.

The invention claimed is:

1. A method of testing an efficacy of a sanitation process, comprising:

providing a first surrogate for a first pathogen, wherein the first surrogate comprises a first taggant chemically bound to a first surrogate carrier, wherein the first surrogate carrier is non-toxic and comprises one or more of a bio-degradable polymer, maltodextrin, salt, starch, a non-water-soluble food grade polymers, a protein, a membrane lipid, a gelatin-based polymer, agar agar, carrageenan, gellan, gelatin, latex, glycerol ester of wood rosin, pectins, carnauba, silica, water-soluble carbohydrate, flour, albumin, casein, a particle bearing a core of a functionally ferromagnetic material, or fixed cells of a formerly living microorganism, wherein the first surrogate has been determined to have degradation rates that match degradation rates of the first pathogen, and wherein the first taggant is formed of a first DNA bar code that has a DNA degradation rate under the first sanitation operation independent of the carrier degradation rate;

applying a first amount of the first surrogate to one or more processing or product surfaces;

subsequently performing the first sanitation operation, whereby a portion of the first surrogate carrier is degraded by the first sanitation operation; and subsequently performing a detection operation to determine a second amount of the first surrogate present on the one or more surfaces after performing the first sanitation operation, wherein determining the second amount is performed by determining an amount of the first DNA bar code present on the one or more surfaces; and determining the efficacy of the sanitation process from a comparison of the second amount to the first amount.

2. The method of claim 1, wherein the first surrogate is applied to one or more surfaces of a food processing facility.

3. The method of claim 2, wherein the first surrogate is applied as an aerosol or a suspension in a liquid spray.

4. The method of claim 1, wherein applying the first surrogate includes applying the first pathogen surrogate to a food product.

5. The method of claim 1, wherein the first sanitation operation includes a wash water process.

6. The method of claim 1, wherein the detection operation includes use of one or more of a polymerase chain reaction (PCR), loop mediated isothermal amplification, or surface enhanced Raman spectroscopy.

7. The method of claim 1, further comprising:

prior to performing the first sanitation operation, providing a second surrogate for the first pathogen, wherein the second surrogate comprises a second taggant chemically bound to a second surrogate carrier, wherein the second surrogate carrier is non-toxic and selected to have a carrier degradation rate comparable to a pathogen degradation rate of the first pathogen under a first sanitation operation, and wherein the second taggant is formed of a second DNA bar code that has a DNA degradation rate under the first sanitation operation independent of the carrier degradation rate;

applying a first amount of the second surrogate to one or more surfaces;

wherein the first and second surrogates have differing degrees of robustness relative to the first sanitation operation, and wherein the detection operation is further performed to determine a third amount of the second surrogates present after performing the first sanitation operation, wherein determining the third amount is performed by determining an amount of the second DNA bar code present on the one or more surfaces.

8. The method of claim 1, wherein the first non-toxic pathogen surrogate carrier includes one or more of maltodextrin, a salt, a starch, a non-water soluble food grade polymer, a protein, or a lipid.

9. The method of claim 1, wherein the first non-toxic pathogen surrogate carrier is a poly(lactic-co-glycolic acid) polymer.

10. The method of claim 1, wherein the first non-toxic pathogen surrogate carrier is a gelatin based carrier.

11. The method of claim 1, wherein the first surrogate includes UV inhibitors.

12. The method of claim 1, wherein the first surrogate includes anti-oxidants.

13. The method of claim 1, wherein the first non-toxic pathogen surrogate carrier includes one or more of carrageenan, carnauba, silica, water-soluble carbohydrate, flour, albumin, casein.

14. The method of claim 1, wherein the first surrogate carrier is a particle bearing a core of a functionally ferromagnetic material.

15. The method of claim 1, wherein the first surrogate includes fixed cells of a formerly living microorganism.

16. The method of claim 1, wherein the first DNA bar code is encapsulated in the first surrogate carrier.

17. The method of claim 1, wherein the first DNA bar code is absorbed by the first surrogate carrier.

18. The method of claim 1, wherein the first DNA bar code is adsorbed onto the first surrogate carrier.

19. The method of claim 1, wherein the first surrogate carrier comprises a food-grade protein.

20. The method of claim 19, wherein the first surrogate carrier comprises a non-water-soluble food-grade protein.

* * * * *